United States Patent [19]

Lin et al.

[11] Patent Number: 5,084,202
[45] Date of Patent: Jan. 28, 1992

[54] ISOCYANATE PREPOLYMERS AND SECONDARY AMINES FROM DISECONDARY AMINES AND ALKYL DIISOCYANATES

[75] Inventors: Jiang-Jen Lin, Houston; George P. Speranza, Austin, both of Tex.

[73] Assignee: Texaco Chemical Company, White Plains, N.Y.

[21] Appl. No.: 377,355

[22] Filed: Jul. 10, 1989

[51] Int. Cl.$^5$ ............................................. C09K 3/00
[52] U.S. Cl. ............................... 252/183.11; 252/182.2
[58] Field of Search ........................... 252/182.2, 183.11

[56] References Cited

U.S. PATENT DOCUMENTS

| | | | |
|---|---|---|---|
| 3,117,999 | 1/1964 | Boettner et al. | 564/505 |
| 3,364,239 | 1/1968 | Speranza | 564/472 |
| 3,626,023 | 12/1971 | Brizgys | 252/183.11 |
| 4,286,014 | 8/1981 | Tanaka et al. | 528/61 |
| 4,417,075 | 11/1983 | Stogryn | 564/505 |
| 4,429,157 | 1/1984 | Disteldorf et al. | 564/446 |
| 4,471,138 | 9/1984 | Stogryn | 564/508 |
| 4,658,005 | 4/1987 | Gras et al. | 528/45 |
| 4,761,465 | 8/1988 | Speranza et al. | 528/45 |
| 4,766,199 | 8/1988 | Takekoshi et al. | 252/183.11 |
| 4,941,991 | 7/1990 | Rajamannan | 252/183.11 |

Primary Examiner—Edward A. Miller
Attorney, Agent, or Firm—Jack H. Park; Kenneth R. Priem; Cynthia L. Kendrick

[57] ABSTRACT

Disclosed are novel isocyanate prepolymers and novel secondary amines, both prepared from alkyl diisocyanates and secondary isopropyl derivatives of polyoxyalkylene diamines. The molar ratios, reaction procedures (i.e. inverse addition of reactants) and solvent determine the products. Most of the products are light colored and nongelled.

The isocyanate prepolymers are useful in the field of polyurethanes and the novel secondary amines are useful in epoxy coatings applications.

5 Claims, No Drawings

ISOCYANATE PREPOLYMERS AND SECONDARY AMINES FROM DISECONDARY AMINES AND ALKYL DIISOCYANATES

Field Of The Invention

This invention relates to products of polyoxyalkylene amines and isocyanates. More particularly this invention relates to a series of new isocyanate prepolymers and secondary amines synthesized from diisocyanates and disecondary amines. Still more particularly, this invention relates to novel compounds having, in one embodiment, active isocyanate terminal groups, two urea linkages, two alkyl groups and ether functionalities and, in another embodiment, terminal secondary amines and internal urea linkages. Both products are prepared by reacting a diisocyanate with an N,N'-diisopropyl derivative of a polyoxyalkylene diamine in the presence of polar solvent. The reactants are essentially the same; therefore molar ratios and techniques in procedure are critical for obtaining an isocyanate prepolymer or a novel secondary amine. Products will differ depending on amine concentration. The reaction is preferably conducted under nitrogen atmosphere at a temperature within the range of about 0° C. to 100° C.

Most of the isocyanate prepolymers were liquid with high viscosity, especially useful in the field of polyurethanes. The novel secondary amines had excellent color and viscosity properties and appeared very useful as epoxy coatings and in polyurea applications. The polyoxyalkylene amine from which the diisopropyl disecondary amine is derived and the particular diisocyanate affect the color and viscosity of the product.

BACKGROUND OF THE INVENTION

The reaction of isocyanates with amines is known in the art and is an extremely fast reaction. It has only been recently that higher molecular weight diamines could be made to react with diisocyanates in a controlled fashion. Work in this area led to the Reaction Injection Molding (RIM) process for the preparation of polyurea plastics.

Reaction of polyisocyanates with polyamines that were soluble or partially soluble in water has often led to gel formation though it might have been expected there would be advantages to carrying out the reaction in water, in that the water would serve as a heat sink.

In contrast to the isocyanate-amine reaction, the reaction of alcohol-isocyanate proceeds at a slower rate. The isocyanate polymers prepared from polyol and isocyanate are well-known and used widely in commercial processes. (see J.H. Saunders and K.C. Frisch, High Polymer Vol. XVI, polyurethanes: Chemistry and Technology (part 1) Interscience publishers (1962)).

In the references discussed below there is information regarding the preparation and use of polyol-isocyanate prepolymers.

Chung et al. disclose in U.S. Pat. No. 4,590,254 a poly(urethane-urea) which is prepared by reverse addition of an isocyanate-terminated prepolymer to an organic medium containing a chain extender such as hydrazine.

In U.S. Pat. No. 4,617,349, Nasu et al. disclosed a urethane resin composition which comprises a polyisocyanate component having from 20/80 to 80/20 of a weight ratio on a solid basis of an α,α,α',α'- tetramethyl-xylylene diisocyanate derivative to a hexamethylene diisocyanate derivative and an acrylic polyol.

In U.S. Pat. No. 4,611,043 there is disclosed a coating composition prepared from (a) an isocyanate terminated prepolymer which comprises the reaction product of at least one polyurethane-forming reagent containing a plurality of isocyanate groups and at least one polyfunctional polyhydric alcohol and (b) dicyclopentenyl alcohol.

The above prepolymers were generally prepared from polyols and diisocyanates using a tin catalyst and elevated reaction temperatures.

U.S. Pat. No. 4,609,718, discloses a coating composition consisting essentially of a linear acrylate-terminated polyurethane oligomer, including urea groups, introduced by the presence in the oligomer of a reaction product with an isocyanate functionality of about 30% to about 90% by weight of the acrylate-terminated oligomer of a polyoxyalkylene diamine having a molecular weight in the range of from about 1000 to about 8000.

It would be a novel method and a distinct advance in the art if a plant could use disecondary amines and alkyl diisocyanates to produce two different products, each a novel composition having very desirable properties for use in various related arts.

Alkyl diisocyanates and derivatives of disecondary amines, including N,N'-diisopropyl JEFFAMINE ® amines, can be used to produce novel isocyanate prepolymers or disecondary amines by varying molar ratio, order of addition and, in some cases, solvent.

SUMMARY OF THE INVENTION

It is an object of the present invention to provide a method of preparing a series of novel isocyanate prepolymers and secondary amines exhibiting desirable structures and arrangements of groups and linkages and also to provide a method which avoids gel formation.

More specifically, in accordance with the present invention, there is provided in the first embodiment a process for the preparation of a series of novel isocyanate prepolymers which comprises reacting a diisocyanate with the secondary isopropyl derivative of a polyoxyalkylenediamine in the presence of a ketone solvent at room temperature and atmospheric pressure. Here the addition of excess diisocyanate to amine is important. The prepolymers generally are nongelled, but of high viscosity. In a second embodiment an excess of disecondary amine derivative is reacted with the diisocyanate in a polar solvent to produce novel secondary amines. The procedures and molar ratio allow the production of less viscous, nongelled products.

The reaction procedures, molar ratios and solvent are important. Where isophorone diisocyanate is reacted with the N,N'-diisopropyl derivative of an amine terminated polyethylene glycol the product can be represented in the first embodiment by:

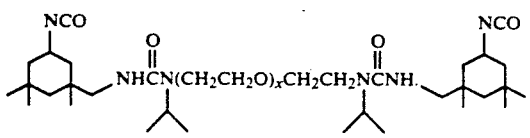

and in the second embodiment by:

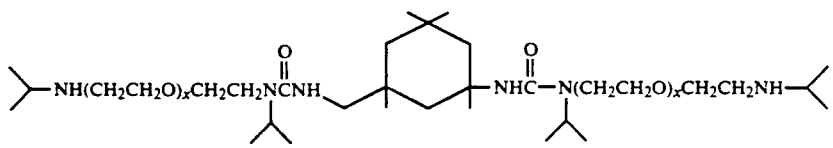

DESCRIPTION OF THE PREFERRED EMBODIMENTS

According to the present invention new secondary amine derived isocyanate prepolymers are formed which contain two active isocyanate terminating groups, two urea linkages, two alkyl groups and ether functionalities and are in the form of a high viscosity liquid. Using the same reactants a secondary amine having terminal secondary amines and containing alkyl and urea functionalities can be obtained by a controllable reaction and without undesirable gel formation. The molar ratio of reactants and inverse addition of isocyanate to excess amine in a polar solvent results in the formation of the novel secondary amines containing alkyl and urea functionalities while, in the first embodiment, where the molar ratio is adjusted to an excess of diisocyanate and the amine is added to the isocyanate in a ketone solvent, the same reactants result in novel isocyanate prepolymers containing polyoxyalkylene amine and alkyl functionalities. The reaction takes place over a period of hours at low temperatures. The amine products are generally light colored liquids with low viscosity. The prepolymers are generally more viscous light colored liquid products.

The novel isocyanate prepolymers and secondary amines of the present invention contain as one of the principle reaction components a diisocyanate of the formula:

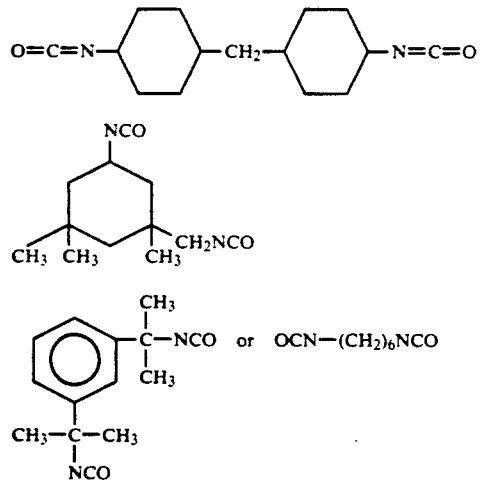

and an appropriate isopropyl secondary amine from the group of disecondary amines having the formula:

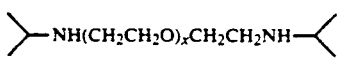

wherein x is a number having an average value of about 1 to about 3.

The novel isocyanate prepolymers of this invention were prepared by the reaction of diisocyanates and disecondary amines in the presence of a polar solvent according to the following:

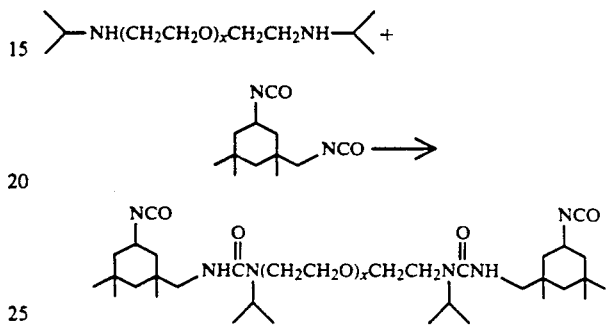

The new secondary amines are prepared according to the following idealized reaction:

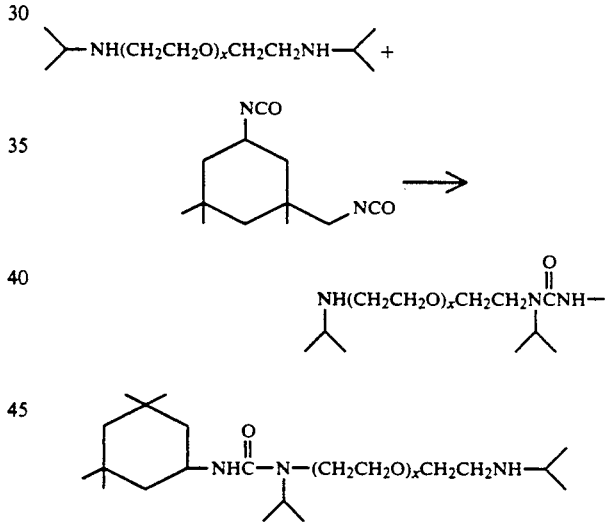

The Diisocyanate

The isocyanate component for the present invention may be any suitable isocyanate having the desired functionality. Diisocyanates are preferred in the process. The organic diisocyanate is preferably an aliphatic or aromatic diisocyanate. Although diisocyanates are preferred, other higher polyisocyanates can be used in combination with diisocyanates and/or monoisocyanates. Examples of suitable aliphatic diisocyanates are aliphatic diisocyanates such as 1,6-hexamethylene diisocyanate, 1,4-cyclohexyl diisocyanate, isophorone diisocyanate, xylylene diisocyanate, m- and p- tetramethylxylylene diisocyanate, 4,4'methylene-bis(cyclohexyl isocyanate), 2,2,4-trimethylhexamethylene diisocyanate, 2,4,4-trimethylhexamethylene diisocyanate and mixtures thereof. Substituted organic polyisocyanates can also be used in which the substituents are nitro, chloro, alkoxy and other groups which are not reactive with hydroxy groups or active hydrogens and provided the substituents do not adversely affect the intended use of the diamine.

Preferred diisocyanates for producing novel secondary amines, are isophorone diisocyanate and tetramethylxylene diisocyanate.

The Isopropyl Secondary Amine Derivative Reactant

In general the disecondary amine starting material may be defined as a derivative of a polyoxyalkylene diamine or triamine. One group of appropriate polyoxyalkylene diamines that may be used are those sold by Texaco Chemical Company as JEFFAMINE ® D-series products having the formula:

$$H_2N-CH-CH_2-[O-CH_2-CH]_x-NH_2$$
$$\qquad\; R' \qquad\qquad\quad R'$$

where R' independently represents H or methyl and x is a number having an average value of about 2 to about 6.

Another group of appropriate polyoxyalkylene diamines that may be used as a source of the disecondary amine derivatives are those sold by Texaco Chemical Co. as JEFFAMINE ® EDR-series products having the formula:

$$H_2N-CH_2-CH_2[-O-CH_2-CH_2]_x-NH_2$$

wherein x is 2 or 3.

Representative products having this structural formula include polyoxythylene diamines produced by Texaco Chemical Co. under the tradename JEFFAMINE ® EDR amines, having the structure above where:

x=2 for JEFFAMINE ® EDR-148
x=3 for JEFFAMINE ® EDR-192

The polyoxyalkylene diamines are alkylated according to the procedures in Patent Application Ser. No. 07/135,798 to produce the N-isopropyl diamine derivatives used in the Examples of this invention.

In that procedure the polyoxyalkylene diamine is reacted with acetone in the presence of a hydrogenation catalyst and hydrogen where the ratio of acetone to amine starting material is within the range of about 1.5 to about 3 mole equivalents of acetone per mole of primary amine group present in the amine reactant.

Solvents

In the method of this invention the solvent is essential for avoiding gel formation.

Suitable solvents are those which are less reactive toward isocyanate groups than amino compounds. Generally suitable solvents are polar or those having a high dielectric constant.

Examples of suitable polar solvents include acetone, isopropanol and methyl t-butyl ether. Among the solvents studied were acetone and i-PrOH. Good results were obtained using with these two solvents. In the method for making prepolymers acetone was preferable.

Preparation Of The Novel Isocyanate Prepolymer

In the first embodiment it has been discovered that a novel isocyanate prepolymer is preferentially formed when an excess of diisocyanate, such as, for example, isophorone diisocyanate or tetramethyl xylene diisocyanate is added to an N,N'-diisopropyl derivative of an amine terminated polyethylene glycol or polypropylene glycol at a temperature within the range of 0° C. to 180° C. and preferably 10° C. to 50° C. for a reaction time within the range of about 1 to about 5 hours.

In this embodiment the molar ratio is important. A ratio of 1 to 4 moles of diisocyanate per mole of disecondary amine will afford desired results and a ratio of 2.1 to 3.0 moles diisocyanate per mole amine is preferred.

The novel prepolymers are generally light colored liquids with high viscosities containing two terminal active isocyanate groups, two urea linkages, two alkyl groups and ether functionalities. Those skilled in the art will see the benefits and applications for a prepolymer possessing such an arrangement of functional groups.

The reaction mixture will comprise an N,N'-diisopropyl disecondary amine which may be generally characterized by the following formula:

$$NH(CH_2CH_2O)_xCH_2CH_2NH$$

wherein x is 2 or 3 and a diisocyanate, such as isophorone diisocyanate, m- and p- tetramethylxylylene diisocyanate or 1,6-hexamethylene diisocyanate etc. More particularly, the diisocyanate can be represented by one of the following formulas:

$$O=C=N+CH_2)_6N=C=O$$

Where isophorone diisocyanate (IPDI) and the N,N'-diisopropyl derivative of an amine terminated polyethylene glycol are used as reactants the product can be represented by the structure:

Preparation of the Novel Secondary Diamines

It has also been discovered in accordance with the present invention that a novel secondary amine product is preferentially formed when a diisocyanate is added to an excess of the isopropyl diamine derivative under nitrogen atmosphere and at a temperature within the range of about 0° C. to 100° C. for a reaction time within the range of about 1 to about 10 hours. Normally, the reaction will go to completion after a reaction time within the range of about 1 to about 4 hours depending on how fast the heat of reaction can be removed.

The reaction is complete when essentially all the isocyanate groups of the alkyl diisocyanates have reacted with amino groups of the diisopropyl secondary amine.

The novel disecondary amines formed by the process of the present invention are generally light colored liquids having a molecular weight within the range of about 200 to 2000 and preferably from 350 to about 1000 and containing alkyl groups and an average of two urea linkages.

A variety of molecular configurations are possible for the novel disecondary amine products of the present invention, depending on the starting materials.

Where isophorone diisocyanate (IPDI) and the N,N'-diisopropyl derivatives of JEFFAMINE ® EDR-148 or EDR-192 are used as reactants, the product can be represented by the structure:

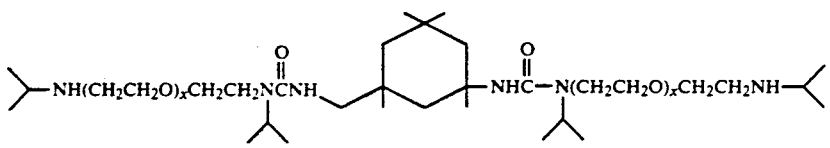

where x=2 for JEFFAMINE ® EDR-148
x=3 for JEFFAMINE ® EDR-192

It has been demonstrated that the inverse addition of the diisocyanate to the amine is essential for obtaining less viscous or nongelled products.

Generally an excess of amine is necessary. The molar ratio of isopropyl secondary amine derivative to diisocyanate reactant is in the range of 2.1 to 3. A range of 2.5 to 3 provides desirable results.

The present invention will be further illustrated by the following Examples which are only for the purpose of illustration and are not to be regarded as limiting the invention in any way.

In Examples 1-9 it will be noted that: (1) new isocyanate prepolymers were made containing JEFFAMINE ® amine and isopropyl (alkyl) groups in the structure; (2) the ratio of isocyanate to amine is the important factor contributing to the product being in liquid form; (3) a ketone solvent is preferred. Other solvents such as diethyl ketone, methyl ethyl ketone are suitable, and (4) the Comparative Examples illustrate the importance of the choice of solvents.

EXAMPLE 1

Adduct of Isophorone Diisocyanate (IPDI) and N,N'-diisopropyl JEFFAMINE ® EDR-148 (3:1 molar ratio)

A 250 ml three-necked flask equipped with a thermometer, Dean-Stark trap, stirrer and nitrogen inlet line was charged with IPDI (66.6 g, 0.3 mole). At room temperature, N,N'-diisopropyl JEFFAMINE ® EDR-148 (23.2 g, 0.1 M) in acetone (60 g) was added dropwise over a 3 hour period. The maximum exothermic temperature at 30° C. was recorded. After finishing the amine addition, the mixture was heated to 130° C. (to remove solvent) and subjected to vacuum (ca. 40mm HG) for 30 minutes. The recovered light-brown liquid was analyzed (86.5 g) for isocyanate content, 4.3 meq/g (calc. 4.4 meq/g) and viscosity 5900 cs/50° C.

EXAMPLE 2

Adduct of Tetramethyl Xylene Diisocyanate (TMXDI) and N,N'-Diisopropyl JEFFAMINE ® EDR 148 (4:1 molar ratio)

A 250 ml three-necked flask equipped with a thermometer, Dean-Stark trap, stirrer and nitrogen inlet line was charged with TMXDI (72.2 g, 0.3 M). At room temperature, N,N'-diisopropyl JEFFAMINE ® EDR-148 (17.4, 0.075 M) in acetone (60 ml) was added dropwise over a 1.5 hour period of time. The mixture was heated slowly to 120° C. to remove solvent and further subjected to vacuum (ca. 40mm Hg) for 30 minutes. The recovered product was transparent, brown liquid (69 g) having analyses of 4.6 meq/g (calc. 5.0 meq/g) for isocyanate and 7400 cs/25° C. for viscosity.

EXAMPLE 3

Adduct of Tetramethyl Xylene Diisocyanate (TMXDI) and N,N'-Diisopropyl JEFFAMINE ® EDR-148 (3:1 molar ratio)

(Comparative with Example 1)

A 250 ml three-necked flask equipped with a thermometer, Dean-Stark trap, stirrer and nitrogen inlet line was charged with TMXDI (73.2 g, 0.3 mole). At room temperature, N,N'-diisopropyl JEFFAMINE ® EDR-148 (23.2 g, 0.1 M) in acetone (60 ml) was added dropwise over a 1.5 hour period of time. The mixture was heated slowly to remove solvent and further subjected to 130° C. under vacuum for 30 minutes. The recovered material was a dark solid.

EXAMPLE 4

Adduct of Isophorone Diisocyanate (IPDI) and N,N'-Diisopropyl JEFFAMINE ® EDR-192 (4:1 molar ratio)

A 500 ml three-necked flask equipped with a thermometer, Dean-Stark trap, stirrer and nitrogen inlet line was charged with IPDI (88.8 g, 0.4 M). The solution of N,N'-diisopropyl JEFFAMINE ® EDR-192 (27.6 g, 0.1 M) in acetone (60 g) was added dropwise over 30 minutes. The exothermic reaction was subsided by ice-/water bath with temperature control at 15°-35° C. during addition. Then the mixture was heated to remove acetone at <130° C. and under vacuum at 130° C. for 15 minutes. The resulting liquid product (112.5 g) was analyzed: isocyanate content 5.0 meq/g (calc. 5.2 meq/g), amine content 0.05 meq/g and viscosity 4800 cs/25° C.

EXAMPLE 5

Adduct of Isophorone Diisocyanate (IPDI) and N,N'-Diisopropyl JEFFAMINE ® EDR-192 (3:1 molar ratio)

A 250 ml three-necked flask equipped with a thermometer, Dean-Stark trap, stirrer and nitrogen inlet line was charged with IPDI (66.6 g, 0.3 M). The solution of N,N'-diisopropyl JEFFAMINE ® EDR-192 (27.6 g, 0.1 M) in acetone (60 g) was added dropwise over 30 minutes at a temperature of 20°≈34° C. The mixture was then heated to remove acetone and subjected to vacuum at 125° C. for 15 minutes. The recovered product (90 g) was a yellow, viscous liquid. The analyses indicated an isocyanate content of 4.2 meq/g (calc. 4.3 meq/g), amine content 0.04 meq/g and viscosity 71,800 cs/25° C.

EXAMPLE 6

Usage of Sample from Example 5, Adduct of IPDI-N,N'-i-Pr₂ EDR-192 (3:1 molar ratio)

The sample of Example 5 (10 g, prepared from IPDI and N,N'-i-propyl EDR-192 4.2 meq/g) and PPG-400 (polypropylene glycol most ≈400, 8.4 g) and catalyst COCURE® 30 (urethane catalyst from Cosan Chemical Corp.) were mixed well and poured into a mold and cured at 95° C. overnight to give a slightly flexible, transparent tough material. The above example was repeated except using 1,4-butanediol (3.8 g) instead of PPG-400, which gave a foam like, white solid with good integrity but brittle.

EXAMPLE 7

Adduct of Isophorone Diisocyanate (IPDI and N,N'-Diisopropyl JEFFAMINE® EDR-192 (2:1 molar ratio)

The experimental procedures of the above Examples were repeated except charging IPDI (66.6 g, 0.3 M), i-Pr₂ EDR-192 (41.4 g, 0.15 M) and acetone (60 g). The reaction conditions were at room temperature for ca. 2.5 hours. After removing solvents, a semi-solid product (96 g) was obtained.

EXAMPLE 8

Attempted Preparation of IPDI and i-Pr₂ EDR-192 Adduct Without Using Solvent (4:1 molar ratio)

A 250 ml three-necked flask equipped with a thermometer, Dean-Stark trap, stirrer and nitrogen inlet line was charged IPDI (88.8 g). At room temperature, diisopropyl JEFFAMINE® EDR-192 (27.6 g) was added dropwise. During this process, a gel-formation was observed. It is evident that a suitable solvent for this reaction is required.

EXAMPLE 9

Attempted Preparation of IPDI and i-Pr₂ EDR-192 in i-ProH Solvent (4:1 molar ratio)

A 250 ml three-necked flask equipped with a thermometer, Dean-Stark trap, stirrer and nitrogen inlet line was charged with IPDI (88.8 g, 0.4 M) and i-ProH (50 ml). Then, N,N'-diisopropyl JEFFAMINE® EDR-192 (27.6 g, 0.1 M) was added dropwise for a 1 hour period of time at RT - 35° C. The solvent was then removed at 130° C. at atmospheric pressure and at reduced pressure. A glossy solid product was obtained. In comparison to acetone solvent, isopropanol is a less suitable solvent.

EXAMPLE 10

Usage of Example 19, (Adduct of IPDI-i-Pr₂ EPR-148

The mixture of Example 19 (15 g) and EPON® 828 (8.7 g) were mixed and cured at 95° C. overnight. The resulting material was a light-colored, transparent, tough and hard solid at room temperature and softened when heated.

EXAMPLE 11

Usage of 6322-53 (Adduct of TMXDI-i-Pr₂ EDR-148)

The mixture of Example 16 (15 g) and EPON® 828 (7.6 g) was cured at 95° C. overnight. The resulting material was soft at elevated temperature and hard but brittle at room temperature.

COMPARATIVE EXAMPLE 12

Adduct of N,N'-diisopropyl EDR-148 and Isophorone Diisocyanate (IPDI) at 2:1 Molar Ratio in Acetone A 250 ml three-necked flask equipped with a thermometer, Dean-Stark trap, stirrer and nitrogen inlet line was charged with IPDI (33.3 g, 0.15 M). Then, the solution of N,N'-diisopropyl EDR-148 (69.6 g, 0.30 M) in 100 g acetone was added dropwise at 23°≈40° C. over a three hour period of time. After the addition, the mixture was heated to 120° C. (maximum temperature) to remove solvent and further subjected to reduced pressure at 120° C. for 20 minutes. The resulting product was a light-colored semi-solid (94 g). The analyses indicated 2.9 meq/g total amine (calc. 2.9 meq/g) and 58,000 cs/50° C. for viscosity.

EXAMPLE 13 (6322-49)

Adduct of N,N'-diisopropyl EDR 192 and IPDI at 2:1 Molar Ratio in Acetone

The same experimental procedures were used as the above example except IPDI (22.2 g, 0.1 M) was employed along with N,N'-diisopropyl EDR-192 (55.2 g, 0.2 M) and acetone solvent (80 g). The resulting product (74.5 g) was a transparent light-yellow liquid with an amine content of 2.68 meq/g (calc. 2.60 meq/g) and a viscosity of 1100 cs at 50° C.

EXAMPLE 14

Adduct of IPDI and N,N'-diisopropyl Bisaminoethyl Ether (BAEE) at 1:3 Molar Ratio in Acetone and Cellusolve Acetate A 250 ml three-necked flask equipped with a thermometer, Dean-Stark trap, stirrer and nitrogen inlet line was charged with IPDI (40 g, 0.13 M) and cellusolve acetate (40 M).

Then, the solution of N,N'-diisopropyl BAEE (68 g, 0.36 M) in acetone (68 ml) was added dropwise at 23°≈31° C. over a 2 hour period of time. The mixture was heated to 130° C. to remove acetone solvent. The resulting product mixture (149 g, containing cellusolve acetate solvent) had an amine content of 2.53 meq/g. The product was a transparent, light-colored liquid.

EXAMPLE 15

Adduct of Tetramethylxylene Diisocyanate and N,N'-diisopropyl EDR-192 (Molar Ratio 1:2) in Acetone A 250 ml three-necked flask equipped with a thermometer, Dean-Stark trap, stirrer and nitrogen inlet line was charged with tetramethylxylene diisocyanate (TMXDI) (24.4 g, 0.1 M), and acetone (30 g). The mixture of N,N'-diisopropyl EDR≈192 (55.2 g, 0.2 M) and acetone (55 g) was added dropwise at 12°-30° C. over 25 minutes. Then, the mixture was heated to 120° C. to remove acetone solvent. The final product mixture was a brown liquid (76.5 g) with a total amine content of 2.47 meq/g and viscosity of 4200 cs/38° C.

EXAMPLE 16

Adduct of TMXDI and N,N'-diisopropyl EDR-148 Molar Ratio at 1:2) in Acetone

The procedures of Example 15 were repeated except using TMXDI (36.6 g, 0.15 M) and acetone (30 g), which was added with i-Pr$_2$ EDR-148 (69.6 g 0.3 M) in acetone (70 g). The resulting product was a viscous brown liquid with analyses of 2.71 meq/g for total amine and viscosity of 3400 cs/50° C.

EXAMPLE 17

Adduct of N,N'-diisopropyl EDR 148 and Isophorone Diisocyanate at 2:1 Molar Ratio in Acetone A 250 ml three-necked flask equipped with a thermometer, Dean-Stark trap, stirrer and nitrogen inlet line was charged with N,N'-diisopropyl EDR-148 (69.6 g, 0.3 M) in acetone (70 g). The solution of isophorone diisocyanate (33.3 g, 0.15 M) in acetone (30 g) was added dropwise over a 15 minutes. period of time. The reaction temperature was kept at 15°≈22° C. by an ice water bath. After completing the addition, the mixture was heated to 130° C. to remove acetone solvent and subjected to reduced pressure at 130° C. for about 1 hour. The resulting product was a viscous, light-colored liquid with the analyses of 4900 cs/50° C. for viscosity and 2.95 meq/g for amine content. In comparison with Example (12), the reverse addition of isocyanate to amine produced a less viscous product which is more desirable for many applications.

EXAMPLE 18

Adduct of IPDI and N,N'-diisopropyl EDR-148 (1:2 Molar Ratio) in i-Propanol

A 250 ml three-necked flask equipped with a thermometer, Dean-Stark trap, stirrer and nitrogen inlet line was charged with IPDI (33.3 g, 0.15 M) and i-propanol (30 g). With stirring and cooling, the solution of N,N'-diisopropyl EDR-148 (69.6 g, 0.3 M) and i-propanol (70 g) was added dropwise at 22°-35° C. over a 1 hour period of time. The mixture was heated to 130° C. to remove i-propanol solvent and further subjected to the reduced pressure for 30 minutes. The resulting product was a transparent, viscous, light-colored liquid. The analyses indicated 2.96 meq/g for total amine content and 4100 cs/50° C. for viscosity.

EXAMPLE 19

Adduct of IPDI and N,N'-diisopropyl EDR-148 (1:2 Molar Ratio in i-Propanol)

In comparison with the previous example, the following example involves a technique of "inverse addition."

A 250 ml three-necked flask equipped with a thermometer, Dean-Stark trap, stirrer and nitrogen inlet line was charged with N,N'-diisopropyl EDR-148 (69.6 g, 0.3 M) and i-propanol (70 g). With stirring and cooling, the solution of IPDI (33.3 g, 0.15 M) in i-propanol (30 g) was added dropwise at ≈25° C. over about a 2 hour period of time. The mixture was then heated to 135° C. to remove solvent and further subjected to the reduced pressure. The resulting product mixture was a light-colored, viscous liquid (100 g). The analyses indicated the content of total amine was 3.09 meq/g and the viscosity was 3000 cs/50° C. The inverse addition of diisocyanate to diamine appeared to give a less viscous product.

EXAMPLE 20

Adduct of PIDI and N,N'-diisopropyl EDR 148 (at 1:2 Molar Ratio) in MTBE

A 250 ml three-necked flask equipped with a thermometer, Dean-Stark trap, stirrer and nitrogen inlet line was charged with N,N'-diisopropyl EDR-148 (34.8 g, 0.15 M) and methyl t-butyl ether solvent (35 g). With stirring and cooling, the solution of IPDI (16.7 g) in MTBE (15 g) was added dropwise at 25°-35° C. (exothermic reaction) over a 1 hour period of time. The mixture was heated to ca. 140° C. to remove solvent and further subjected to the reduced pressure. The resulting product (46 g) was a light-colored, viscous liquid. The analyses showed an amine content of 3.38 meq/g and viscosity of 4100 cs/38° C.

What is claimed is:

1. A composition comprising 20% to 80% by weight N,N'-diisopropyl disecondary polyoxyalkylene amine and 80% to 20% by weight diisocyanate wherein the N,N'-diisopropyl disecondary amine is derived from a polyoxyalkylene amine having the formula:

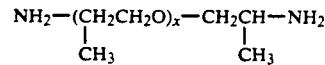

wherein x has a value of 2 to 6 and the diisocyanate is selected from the group consisting of isophorone diisocyanate, tetramethylxylene diisocyanate, 4,4'-methylene-bis-(cyclohexylisocyanate) and xylenediisocyanate.

2. The composition of claim 1 wherein the N,N'-diisopropyl disecondary amine is selected from the group consisting of N,N'-diisopropyl diethylene glycol diamine, N,N'-diisopropyl triethylene glycol diamine, N,N'-diisopropyl tetraethylene glycol diamine.

3. The composition of claim 1 wherein there is an excess of diisocyanate of about 1 to 4 moles of diisocyanate per mole of disecondary amine.

4. The composition of claim 3 wherein the molar ratio is about 2.1 to 3.0 moles of diisocyanate per mole amine.

5. The composition of claim 1 further comprising a disecondary amine formed by the addition of the diisocyanate to the amine in the presence of a solvent selected from the group consisting of acetone, isopropanol and MTBE.

* * * * *